United States Patent [19]

Sugimoto

[11] Patent Number: 4,624,917
[45] Date of Patent: Nov. 25, 1986

[54] PROCESS FOR THE PRODUCTION OF HUMAN T-CELL GROWTH FACTOR

[75] Inventor: Kaname Sugimoto, Okayama, Japan

[73] Assignee: Kabushiki Kaisha Hayashibara Seibutsu Kagaku Kenkyujo, Okayama, Japan

[21] Appl. No.: 572,616

[22] Filed: Jan. 23, 1984

Related U.S. Application Data

[63] Continuation of Ser. No. 349,692, Feb. 17, 1982, abandoned.

[51] Int. Cl.$^4$ .................. C12P 21/00; C12N 15/00; C12N 5/00; C12N 5/02
[52] U.S. Cl. .................. 435/68; 435/172.2; 435/240; 435/241; 435/284; 435/948; 530/351; 935/106; 935/109
[58] Field of Search .................. 435/1, 6, 172.2, 240, 435/241, 68, 948, 248, 245, 286, 284, 172.3; 436/548; 924/85-87; 260/112 R, 112 B; 935/106, 109; 530/351

[56] References Cited

U.S. PATENT DOCUMENTS

| | | | |
|---|---|---|---|
| 4,242,460 | 12/1980 | Chick et al. | 435/284 |
| 4,276,282 | 6/1981 | Sugimoto et al. | 424/85 |
| 4,285,929 | 8/1981 | Sugimoto et al. | 424/85 |
| 4,328,207 | 5/1982 | Sugimoto | 424/85 |
| 4,377,513 | 3/1983 | Sugimoto et al. | 26/112 R |
| 4,383,034 | 5/1983 | Sugimoto | 435/70 |
| 4,383,035 | 5/1983 | Sugimoto | 435/70 |
| 4,383,036 | 5/1983 | Sugimoto | 435/70 |

OTHER PUBLICATIONS

Pattillo, Hormone Synthessi and Function in vitro, *Growth, Nutrition and Metabolism of Cells in Culture*, 1972, Academic Press N.Y., 225-227.

Bordelon et al., Human Glycoprotein Hormone Production in Human-Human and Human-Mouse Somatic Cell Hybrids, *Chem. Abs.*, vol. 86, p. 53093.

Fleischer, Induction of T-Cell Growth Factor Synthesis in Human Peripheral Blood Lymphocytes by Staphylococcal Protein A, J. of Imm. Methods., 47 (1981), 199-200.

Kapp et al., J. Exp. Med., vol. 152, 235-240, Jul. 1980.

Okada et al., PNAS, vol. 78, No. 12, 7717-7727, Dec. 1981.

B. Lewin, *Gene Expression*, 1980, Wiley and Sons, N.Y., pp. 259-265.

J. Ponten et al., "Morphological Virological Investigation of Human Tissue Culture Transformed with SV$_{40}$", *Journal of Cellular and Comparative Physiology*, vol. 61, pp. 145-154 (1963).

Peterson, J. A. et al., "Expression of Differentiated Functions in Hepatoma Cell Hybrids; Induction of Mouse Albumin Production in Rat Hepatoma-Mouse Fibroblast Hybrids", *Proc. Nat. Acad. Sci. USA*, vol. 60, #3, 571-575 (1972).

Malawista, S. E. et al., "Expression of Differentiated Functions in Hepatoma Cell Hybrids: High Frequency of Induction of Mouse Albumin Production in Rat Hepatoma-Mouse Lymphoblast Hybrids", *Proc. Nat. Acad. Sci. USA*, vol. 71, #3, 927-931 (1974).

Narimatsu, H., "T-Cell Growth Factor (TCGF) and Its Applications", *The Metabolism*, vol. 17, pp. 2063-2077 (1980).

Sekiguchi, M. et al., "List of Human Cancer Cell Lines Established and Maintained in Japan", *The Tissue Culture*, vol. 6, No. 13, pp. 527-546 (1980).

Gillis, S. et al., *J. Immunology*, vol. 120, pp. 2027-2032 (1978).

Bordelon, M. R. et al., "Human Glycoprotein Hormone Production in Human-Human and Human-Mouse Somatic Cell Hybrids", *Experimental Cell Research* 103 (1976), 303-310.

*Primary Examiner*—Sidney Marantz
*Assistant Examiner*—Patricia L. DeSantis
*Attorney, Agent, or Firm*—Browdy and Neimark

[57] ABSTRACT

The present invention relates to a process for the production of human T-cell growth factor (abbreviated as "hTCGF" hereinafter). More precisely, the present invention relates to an improved process for the mass-production of hTCGF, comprising transplanting human cells capable of producing hTCGF to a non-human warm-blooded animal, multiplying said cells while allowing the cells to receive the nutrient body fluid supplied from the animal, and producing hTCGF in the multiplied human cells. By the practice of the present invention, a much larger amount of hTCGF, i.e., about 2-10-fold or more larger than that obtained by conventional processes, can be easily obtained; thus, hTCGF in an amount sufficient to carry out various clinical treatments can be easily provided by the present invention.

20 Claims, No Drawings

PROCESS FOR THE PRODUCTION OF HUMAN T-CELL GROWTH FACTOR

This application is a continuation of application Ser. No. 349,692 filed Feb. 17, 1982, abandoned.

The present invention relates to a process for the production of hTCGF(human T-cell growth factor).

hTCGF is a hormone-like, proteinaceous substance, usually prepared from human serum, which stimulates the growth of human T-cells and is, therefore, classified under the family of human multiplication-stimulating activities.

T-cells are lymphocytes which play an important role in in vivo cellular immunity, e.g., delayed hypersensitivity and antitumor immunity.

Since hTCGF stimulates the growth of such T-cells and activates them, it would have a promising potential in therapeutic study and immunotherapy of human diseases, e.g., asthma and malignant tumor, in addition to its current use as an in vitro growth activator of T-cells: thus, establishment of hTCGF mass-production has been in great expectation.

As described by Hisashi NARIMATSU, *The Metabolism*, Vol. 17 pp. 2063-2077 (1980), "T-cell Growth Factor (TCGF) and Its Applications", TCGF is also called "Interleukin" and acts non-species-specifically. Although the non-species-specificity suggests that a TCGF from non-human animal cell origin may be used in place of hTCGF, such replacement has a potential of eliciting undesirable antigen-antibody reaction, e.g., anaphylactic-shock.

Consequently, the use of hTCGF originated from live human cells, in therapy of human diseases is preferable from the point of view of safety because there is no fear that it will elicit undesirable immunoreaction.

Although it has been well known that human serum is a good source for the production of hTCGF, sufficient supply of human serum at a low-cost is very difficult because human serum is only obtained by separation from fresh human blood, and its storage is very difficult.

Because of the above described reasons, no industrial-scale production of hTCGF in an amount sufficient to carry out prophylactic and therapeutic treatments of human diseases has been realized.

The present inventor has investigated processes for the production of hTCGF which can be carried out easily on an industrial-scale.

These efforts have resulted in the unexpected finding that hTCGF production attained with the use of human cells multiplied in a non-human warm-blooded animal is much higher, i.e., about 2-10-fold or more higher, than that attained with the use of human cells multiplied by the in vitro tissue culture method.

More particularly, the present invention relates to an improved process for the production of hTCGF, characterized by transplanting human cells capable of producing hTCGF to a non-human warm-blooded animal, multiplying therein or thereon the human cells while allowing the animal to supply the cells with its nutrient body fluid, and producing hTCGF in the multiplied human cells.

Besides providing a great amount of hTCGF, the process according to the present invention requires no, or much less, nutrient medium containing expensive serum, and renders the maintenance of the culture medium during the cell multiplication much easier than in the case of in vitro tissue culture. An effective multiplication of human cells capable of producing hTCGF can be easily performed by directly transplanting the cells into a non-human warm-blooded animal, or, alternatively, placing the cells in a conventional-type diffusion chamber devised to receive the nutrient body fluid of the animal, while feeding the animal in the usual way.

Furthermore, the process according to the present invention provides a stabler and higher cell multiplication, and a higher hTCGF production per cell, than in vitro tissue culture.

The human cells usable in the present invention are those which are capable of producing hTCGF and multiplying in a non-human warm-blooded animal upon transplantation thereto. For example, normal human cells, such as human peripheral blood, human spleen cells and human tonsil cells; human carcinoma cells, such as human tonsillar abscess cells, human liver carcinoma cells and human lung carcinoma cells; and established cell lines of the above cells, are all favorably feasible in the present invention. The established cell line may be selected from KS-5, MOLT-3, MT-1, Mono-1 and OUMS-19, as described, for example, in *The Tissue Culture*, Vol. 6, pp. 527-546 (1980).

Especially, the use of an established human cell line which can be readily subjected to sub-culture, in which a high hTCGF-production coding gene can be introduced by means of cell fusion technique using polyethylene glycol or Sendai virus, or by gene recombinant technique using ligase, restriction enzyme and DNA polymerase, advantageously results in a higher cell multiplication rate, and higher hTCGF production per cell, i.e., about 2-10-fold or more higher.

Furthermore, since transplantation of such human cell lines into non-human warm-blooded animals results in the formation of massive tumors which can be easily disaggregated and are hardly mixed with the host animal cells, the harvest of the live multiplied human cells can be easily carried out.

For such objectives, human lymphoblastoid lines derived from human leukaemia or human malignant lymphoma, e.g., Namalwa, BALL-1, NALL-1, TALL-1 and JBL, are all advantageously usable.

As to the non-human warm-blooded animals usable in the present invention, any animals may be used so far as the human cells multiply therein; for example, fowls such as chicken or pigeon, and mammalians such as dog, cat, monkey, goat, pig, cow, horse, rabbit, guinea pig, rat, hamster, mouse or nude mouse.

Since transplantation of the human cells into such non-human warm-blooded animals results in the formation of undesirable immunoreaction, the use of an animal in the possible youngest stage is desirable; for example, egg, embryo, foetus, or newborn or infant animal.

In order to reduce the immunoreaction as much as possible, prior to the transplantation the animal may be treated with about 200-600 rem X-ray or γ-ray irradiation, or injected with antiserum or immunosuppressant.

When nude mouse is used as the host animal, since it exhibits less immunoreaction even when in its adulthood, any established human cell line can be readily transplanted and multiplied therein without such pretreatment.

Furthermore, repeated transplantation may be carried out using a combination of different non-human warm-blooded animals both to stabilize the cell multiplication and to further enhance the hTCGF production. For example, the objectives may be attained first by transplanting the human cells into a hamster and allowing the cells to multiply therein, then retransplanting the multiplied human cells into a nude mouse. The repeated transplantation may be carried out with non-human warm-blooded animals of the same class or order, as well as those of the same species or genus.

As to the sites of the animal to which the human cells are transplantable, the human cells can be transplanted to any site of the animal so far as the transplanted human cells multiply therein; for example, in the allantoic cavity, or intravenously, intraperitoneally or subcutaneously.

Instead of directly transplanting the human cells into a non-human warm-blooded animal, any of the established human cell lines can be easily multiplied by embedding, e.g., intraperitoneally, in a non-human warm-blooded animal a conventional-type diffusion chamber of various shapes and sizes, equipped with a membrane filter, ultra-filter or hollow fiber having a nominal pore size of about $10^{-7}$–$10^{-5}$ m, which prevents the contamination of the chamber with the host animal cells and allows the animal to supply the human cells with its nutrient body fluid.

Furthermore, the chamber can be, if necessary, placed, e.g., on the animal body, to allow its nutrient body fluid to circulate from the animal body through the chamber, and devised both to enable the observation of the human cells through transparent side-window(s), equipped on the chamber wall(s), and to enable a quick exchange of the chamber with a fresh chamber; thus, the cell multiplication can be continued over the life span of the host animal to further augment the cell production per animal without sacrifice of the host animal.

When such diffusion chamber is used, since the transplanted human cells do not directly contact with the host animal cells, any non-human warm-blooded animal can be used for the multiplication of the human cells without fear of eliciting undesirable immunoreaction, and the multiplied human cells can be easily harvested.

Feeding of the non-human warm-blooded animal can be advantageously carried out in the usual way, and does not require any special cares even after the transplantation.

Maximum cell multiplication may be usually obtained 1–20 weeks after the transplantation. When the human cell transplanted into the animal is an established human tumor line or human lymphoblastoid line, the maximum cell multiplication may be obtained 1–5 weeks after the transplantation due to their higher multiplication rates.

It has been confirmed that the number of the human cells obtained by the above is up to about $10^7$–$10^{12}$ cells per animal or more. In other words, by the practice of the present invention, the number of the human cells may increase to about $10^2$–$10^7$-fold or higher, which is about $10^1$–$10^6$-fold or more higher than that obtained by in vitro tissue culture method; thus, the human cells obtained as above can be used for the production of hTCGF according to the present invention.

As to the method for the hTCGF production with the human cells, any method can be employed in the invention so far as hTCGF is released thereby. For example, after harvesting the human cells multiplied in ascite in suspension, or extracting and disaggregating the massive tumor, formed subcutaneously, the human cells are then suspended in a nutrient medium, prewarmed to about 20°–40° C., to give a cell concentration of about $10^4$–$10^8$ cells per ml, and incubated therein at this temperature to produce hTCGF.

In the course of the incubation, the nutrient medium may be augmented, if necessary, with an hTCGF inducer. Usable hTCGF inducers are those which induce the production of hTCGF in the human cells multiplied in the non-human warm-blooded animal. The hTCGF inducers may be selected from conventional inducers, e.g., mitogens, such as phytohaemagglutinin, concanavalin A, pokeweed mitogen, lipo-polysaccharide and bacteria; virus; nucleic acid; and poly-nucleotide.

During the hTCGF production, the culture medium may be augmented also with an hTCGF stabilizing agent in order to stabilize the hTCGF formed and further enhance the hTCGF production.

The hTCGF thus obtained can be easily harvested by purification and separation methods using conventional procedures, e.g., salting-out, dialysis, filtration, centrifugation, concentration and lyophilization. If a highly-purified hTCGF preparation is desirable, a preparation of the highest purity can be obtained by the above described procedures in combination with other conventional procedures, e.g., adsorption and desorption with ion exchanger, gel filtration, affinity chromatography, isoelectric point fractionation and/or electrophoresis.

The hTCGF obtained according to the present invention is not contaminated with pyrogen and/or hepatitis virus, as well as being immunologically identical with that obtained from human serum by conventional processes; thus, the hTCGF can be favorably used alone or in combination with one or more agent, e.g., vitamin, hormone and/or carcinostatic agent, for internal or injection administration in the prophylactic and/or therapeutic treatment of human diseases.

Throughout the whole SPECIFICATION, all hTCGF titers were determined by a modification of $^3$H-thymidine incorporation assay previously developed by Gillis S. et al., *J. Immunology*, Vol. 120, pp. 2027–2932 (1978). After placing thymus cells of BALB/c mouse in micro plates to give a cell concentration of 100$\mu$ liters ($10^5$ cells) per well, with 100$\mu$ liters of hTCGF solutions were added to the micro plates, with serial dilutions, and the mixtures were incubated therein at 37° C. for two days. Thereafter, to the micro plates were added 0.5 $\mu$Ci of $^3$H-thymidine per well, and four hours later the incorporated $^3$H-thymidine was assayed by a liquid scintillation counter. One unit of hTCGF titer is defined as the dilution of an hTCGF sample that gives a scintillation count of 5,000 cpm.

The process according to the present invention will be further described by reference to the following EXAMPLEs. However, it is intended that these will in no way limit or define the scope of the invention.

EXAMPLE 1

T-cell type human lymphoblastoid line, MT-1, derived from human peripheral blood, was transplanted intraperitoneally into adult nude mice, and the animals were then fed in the usual way for three weeks.

After extracting the resultant massive tumors, formed intraperitoneally, about 10 g each, they were disaggregated by mincing and suspending in a physiological saline solution containing trypsin.

After washing the human cells with serum-free RPMI 1640 medium (pH 7.2), the cells were resuspended in a fresh medium of the same composition to give a cell concentration of about $1 \times 10^5$ cells per ml, and incubated therein at 37° C. for three days to produce hTCGF.

After completion of the incubation, the culture medium was centrifuged at about 8,000 rpm for 30 minutes, and the hTCGF titer in the resultant supernatant was assayed. The hTCGF production was about 1,600 units per 100µ liter cell suspension.

A control experiment was carried out as follows: the human lymphoblastoid line, MT-1, was cultivated in vitro at 37° C. in Eagle's medium (pH 7.2), supplemented with 1 v/v % foetal calf serum and 20 v/v % meat extract, and the multiplied human cells were then treated similarly as above to produce hTCGF.

The hTCGF production was only about 40 units per 100µ liter cell suspension.

EXAMPLE 2

Disaggregated human tonsillar abscess cells, obtained by extracting from a tonsillar abscess patient, and mincing, and a Namalwa human lymphoblastoid line were suspended together in a salt solution, containing 140 mM NaCl, 54 mM KCl, 1 mM $NaH_2PO_4$ and 2 mM $CaCl_2$, to give respective cell concentrations of about $10^3$ cells per ml. To the cell suspension was further added under ice-chilled conditions a fresh salt solution of the same composition but additionally containing UV-irradiation preinactivated Sendai virus, and about 5 minutes later the mixture was transferred into a 37° C. incubator. The mixture was incubated therein for about 30 minutes to effect cell fusion, introducing the hTCGF-producibility of the MT-1 line into the Namalwa cells.

Thereafter, the resultant hybridized Namalwa cells were transplanted intraperitoneally into adult nude mice, and the animals were fed in the usual way for five weeks.

The resultant massive tumors, formed intraperitoneally, about 15 g each, were extracted, and treated similarly as in EXAMPLE 1 to produce hTCGF, except that the serum-free RPMI 1640 medium contained 1 µg phytohaemagglutinin per ml.

The hTCGF production was about 5,800 units per 100µ liter cell suspension.

In a control experiment, wherein the hybridized Namalwa cells were cultivated in vitro similarly as in the control experiment of EXAMPLE 1, and the multiplied human cells were subjected to hTCGF production, the hTCGF production was only about 90 units per 100µ liter cell suspension.

EXAMPLE 3

After injecting antiserum, prepared from rabbit according to conventional methods, into newborn hamsters to reduce their immunoreaction, there was transplanted subcutaneously into the animals a JBL human lymphoblastoid line in which the hTCGF-producibility of the human tonsillar abscess cells was introduced similarly as in EXAMPLE 2. The animals were fed in the usual way for three weeks.

After extracting the resultant massive tumors, formed subcutaneously, about 18 g each, the cells were treated similarly as in EXAMPLE 1 to produce hTCGF, except that the serum-free RPMI 1640 medium was replaced with Eagle's medium (pH 7.2) supplemented with 20 v/v % meat extract and concanavalin A in an amount of 50 µg per ml medium. The hTCGF production was about 12,000 units per 100µ liter cell suspension.

In a control experiment, wherein the hybridized JBL cells were cultivated in vitro similarly as in the control experiment of EXAMPLE 1, and the multiplied human cells were then subjected to hTCGF production, the hTCGF production was only about 150 units per 100µ liter cell suspension.

EXAMPLE 4

In newborn rats was transplanted intravenously a hybridized Ball-1 human lymphoblastoid line in which the hTCGF-producibility of the human tonsillar abscess cells was introduced similarly as in EXAMPLE 2. The animals were then fed in the usual way for four weeks. After extracting the resultant massive tumors, about 35 g each, the human cells were treated similarly as in EXAMPLE 2 to produce hTCGF. The hTCGF production was about 5,300 units per 100µ liter cell suspension.

In a control experiment, wherein the hybridized BALL-1 cells were cultivated in vitro, and the multiplied human cells were then subjected to hTCGF production, the hTCGF production was only about 110 units per 100µ liter cell suspension.

EXAMPLE 5

After irradiating adult mice with about 400 rem γ-ray to reduce their immunoreaction, the animals were then transplanted subcutaneously with a monocytic-macrophage type established Mono-1 human cell line derived from human peripheral blood, and fed in usual way for four weeks.

After extracting the resultant massive tumors, formed subcutaneously, about 20 g each, the human cells were then treated similarly as in EXAMPLE 3 to produce hTCGF. The hTCGF production was about 3,500 units per 100µ liter cell suspension.

In a control experiment, wherein the Mono-1 line was cultivated in vitro, and the multiplied human cells were then subjected to hTCGF production, the hTCGF production was only about 30 units per 100µ liter cell suspension.

EXAMPLE 6

After placing a cell suspension of a T-cell type MT-1 human lymphoblastoid line derived from human peripheral blood, in physiological saline solution into a plastic cylindrical diffusion chamber of about 10 ml inner volume, equipped with a membrane filter having a nominal pore size of about 0.5µ, the chamber was embedded intraperitoneally in an adult rat. The rat was fed in the usual way for four weeks, and the chamber was removed.

The cell density obtained by the above was about $10^9$ cells per ml, which was about $10^2$-fold higher or more than that obtained in the in vitro tissue culture method using a $CO_2$ incubator.

The human cells thus obtained were treated similarly as in EXAMPLE 3 to produce hTCGF. The hTCGF production was about 3,200 units per 100µ liter cell suspension.

EXAMPLE 7

A Ball-1 human lymphoblastoid line in which the hTCGF-producibility of human tonsillar abscess cells was introduced similarly as in EXAMPLE 4, was transplanted in allantoic cavities of embryonated eggs which had been preincubated at 37° C. for five days, and the eggs were then incubated at this temperature for an additional one week.

The multiplied human cells were collected from the eggs, and treated similarly as in EXAMPLE 1 to produce hTCGF. The hTCGF production was about 2,400 units per 100μ liter cell suspension.

What is claimed is:

1. In a process for producing human T-cell growth factor (hTCGF) which comprises culturing human cells capable of producing hTCGF on an in vitro nutrient culture medium under conditions which permit accumulation of a substantial amount of hTCGF, and recovering the accumulated hTCGF from the culture, the improvement whereby the hTCGF production can be extremely enhanced, wherein said human cells capable of producing hTCGF are obtained by the process comprising:

fusing parent human cells inherently capable of producing hTCGF with a human B-lymphoblastoid line to obtain a hybridoma line having an hTCGF producibility higher than that of the parent human cells;

implanting said hybridoma line in an immunodeficent or immunosuppressed non-human warm-blooded animal;

feeding the animal to allow said hybridoma line to utilize the nutrient body fluid of the animal for its multiplication; and extracting and disaggregating the resultant tumor formed in the animal.

2. A process according to claim 1, wherein said parent human cells are human T-cell lymphoblastoid cells.

3. A process according to claim 1, wherein said parent human cells are human tonsillar abscess cells.

4. A process according to claim 1, wherein said parent human cells are human monocytic-macrophage cells.

5. A process according to claim 1, wherein said parent human cells are those derived from human peripheral blood.

6. A process according to claim 1, wherein said parent human cells are selected from the group of cell lines consisting of KS-5, MOLT-3, MT-1, Mono-1 and OUMS-19.

7. A process according to claim 1, wherein said human B-lymphoblastoid line is of leukemic origin.

8. A process according to claim 1, wherein said human B-lymphoblastoid line is a member selected from the group of cell lines consisting of Namalwa, BALL-1, and JBL.

9. A process according to claim 1, wherein said fusing step comprises:

suspending said parent human cells inherently capable of producing hTCGF together with said human B-lymphoblastoid line in a solution containing an effective amount of a cell fusion inducing agent;

allowing the resultant cell suspension to stand for a period sufficient to effect cell fusion; and selecting or cloning a hybridoma line having an hTCGF producibility higher than that of said parent human cells.

10. A process according to claim 9, wherein said cell fusion inducing agent is selected from the group consisting of an inactivated Sendai virus and polyethylene glycol.

11. In a process for producing human T-cell growth factor (hTCGF) which comprises culturing human cells capable of producing hTCGF on an in vitro nutrient culture medium under conditions which permit accumulation of a substantial amount of hTCGF, and recovering the accumulated hTCGF from the culture, the improvement whereby the hTCGF production can be extremely enhanced, wherein said human cells capable of producing hTCGF are obtained by the process comprising;

fusing parent human cells inherently capable of producing hTCGF with a human B-lymphoblastoid line to obtain a hybridoma line having an hTCGF producibility higher than that of the parent human cells;

suspending said hybridoma line in a diffusion chamber in which the nutrient body fluid of a non-human warm-blooded animal can be supplied to said hybridoma;

embedding or placing said diffusion chamber in or on a non-human warm-blooded animal in a manner such that the nutrient body fluid of the animal is supplied to said hybridoma line within said diffusion chamber;

feeding the animal to allow said hybridoma line to utilize said nutrient body fluid for its multiplication; and harvesting the multiplied hybridoma cells from the diffusion chamber.

12. A process according to claim 11, wherein said parent human cells are human T-cell lymphoblastoid cells.

13. A process according to claim 11, wherein said parent human cells are human tonsillar abscess cells.

14. A process according to claim 11, wherein said parent human cells are human monocytic-macrophage cells.

15. A process according to claim 11, wherein said parent human cells are those derived from human peripheral blood.

16. A process according to claim 11, wherein said parent human cells are selected from the group of cell lines consisting of KS-5, MOLT-3, MT-1, Mono-1 and OUMS-19.

17. A process according to claim 11, wherein said human B-lymphoblastoid line is of leukemic origin.

18. A process according to claim 11, wherein said human B-lymphoblastoic line is a member selected from the group of cell lines consisting of Namalwa, BALL-1, and JBL.

19. A process according to claim 11, wherein said fusing step comprises:

suspending said parent human cells inherently capable of producing hTCGF together with said human B-lymphoblastoid line in a solution containing an effective amount of a cell fusion inducing agent;

allowing the resultant cell suspension to stand for a period sufficient to effect cell fusion; and selecting or cloning a hybridoma line having an hTCGF producibility higher than that of said parent human cells.

20. A process according to claim 19, wherein said cell fushion inducing agent is selected from the group consisting of an inactivated Sendai virus and polyethylene glycol.

* * * * *